United States Patent

Yakshin et al.

[11] 4,004,450
[45] Jan. 25, 1977

[54] DEVICE FOR MEASURING IMPACT PULSES

[76] Inventors: Alexandr Sergeevich Yakshin, ulitsa Malaya Filevskaya, 66, kv. 104; Oleg Nikolaevich Novikov, ulitsa Kuznetsky most, 18/7, kv. 6; Dmitry Alexeevich Grechinsky, ulitsa Tolbukhina, 8, korpus 2, kv. 48; Viktor Alexandrovich Klochko, ulitsa Oktyabrskaya, 38, kv. 374; Viktor Georgievich Rygalin, 3 Dorozhny proezd, 5, korpus 2, kv. 103, all of Moscow, U.S.S.R.

[22] Filed: Dec. 15, 1975

[21] Appl. No.: 640,710

[30] Foreign Application Priority Data

Dec. 19, 1974 U.S.S.R. ............................. 2087064

[52] U.S. Cl. ...................................... 73/12; 73/71.4; 73/492
[51] Int. Cl.² .......................... G01N 3/30; G01M 7/00
[58] Field of Search ......... 73/12, 71.2, 71.4, 517 R, 73/492; 324/99 D, 103 P; 235/151.3, 151.31

[56] References Cited
UNITED STATES PATENTS

| | | |
|---|---|---|
| 3,780,274 | 12/1973 | Thompson et al. ............ 235/151.31 |
| 3,833,797 | 9/1974 | Grobman et al. .............. 235/151.3 |
| 3,930,248 | 12/1975 | Keller ............................ 235/151.3 |

*Primary Examiner*—James J. Gill
*Attorney, Agent, or Firm*—Lackenbach, Lilling & Siegel

[57] ABSTRACT

A device for measuring impact pulses wherein an acceleration pickup converts the mechanical vibrations of an object into electric signals passing through an amplifier unit to a meter for measuring the parameters of the impact pulse. This meter comprises two null-indicators, one of which is connected electrically and directly with the amplifier unit while the other one is connected across a voltage divider connected to a source of a reference voltage, two pulse shapers connected to the null-indicators, two AND-NOT logical elements connected with the pulse shapers and a H.F. pulse generator. The meter comprises one more AND-NOT logical element connected with one of said AND-NOT logical elements and with the most significant and least significant decades, the least significant decade being connected with the other one of said AND-NOT logical elements. Further, said meter comprises a digital-to-analog converter connected with the most and least significant decades and null-indicators, and an indicator connected to said most and least significant decades.

4 Claims, 7 Drawing Figures

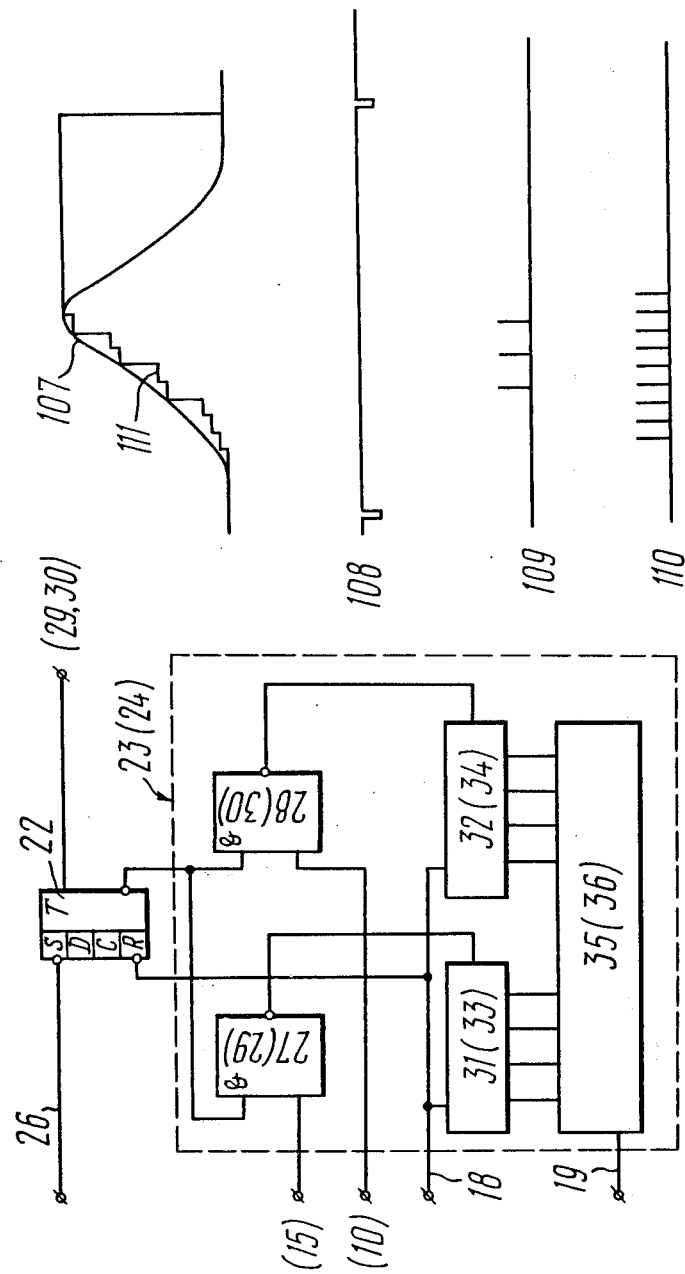

DEVICE FOR MEASURING IMPACT PULSES

The present invention relates to devices for measuring parameters of impact overloads and, more particularly, to devices for measuring impact pulses, for example, for measuring peak values of an impact pulse, impact pulse rise and decay areas characterizing the speed of collision and recoil of colliding objects and the total area of the impact pulse characterizing total speed change in the course of an impact pulse.

The study of impact processes belongs to one of the most vital problems involving the assessment of the behaviour of various objects in all types of impact loading which causes internal stresses, deformation, breaking of bonds and movements inside a material.

In order to estimate an effect of an impact load on an object one must possess comprehensive information about the nature and conditions of the dynamic action: the peak value of acceleration, the duration of rise, decay and total duration of an impact pulse, the shape of said pulse, speeds of collision and recoil, the total speed change in the course of the impact pulse and the value of elasto-plastic strains.

This information will also guarantee the repeated reproducibility of a given pulse under laboratory conditions.

Until recently impact processes have been measured with the aid of the analog equipment which could, as a rule, provide only for measurement of a peak value of an impact pulse. The procurement of other information called for additional deciphering and processing of the impact oscillograms which reduced considerably the rate of date transmission and hindered the timely corrections of the test procedures, particularly while developing new materials or structures.

Also known in the previous art is a device for measuring impact pulses wherein the acceleration pickup converts the mechanical vibrations of an object into electric signals delivered through an amplifier unit to the device for measuring parameters of an impact pulse. This device measures the peak value of the impact pulse.

The appliance for measuring parameters of an impact pulse in said device is made in the form of an analog voltage meter comprising an electrometer stage and an oscilograph and measurement is performed by comparing a pulse memorized on the oscilograph screen with a pulse received from an additional pulse generator.

As a result, said device is characterized by serious errors in measuring parameters of the impact pulse and by limited functional capabilities. The use of the analog devices for measuring a peak value of an impact pulse involves big measuring errors especially in measuring pulses having a complex shape.

The above-mentioned device measures only one parameter of the impact pulse, viz., its peak value.

With the growing range of circuit components including integral logical and analog microcircuits it has become possible to build digital impact-measuring instruments characterized by a wide range of functions, high authenticity and reliability of information and a possibility of communication with electronic digital computers for subsequent analysis of the measured impact processes.

An object of the present invention lies in providing a device for measuring impact pulses which will ensure high-accuracy measurements of several impact pulse parameters, such as the peak value of an impact pulse and its rise, decay and total areas which characterize the speed of collision and recoil and the total speed change of colliding objects, these being the most important parameters in studying the properties of objects suffering impact overloads.

This object is accomplished by providing a device for measuring impact pulses in which an acceleration pickup converts mechanical vibrations of an object into electric signals passing through an amplifier unit to a meter for measuring the parameters of an impact pulse wherein, according to the invention, the meter for measuring the parameters of the impact pulse comprises first and second null-indicators, one input of the first null-indicator being electrically connected with the amplifier unit and one input of the second null-indicator is electrically connected with the same amplifier unit across a voltage divider connected to a source of reference voltage, first and second pulse shapers whose inputs are connected to the outputs of the first and second null-indicators, respectively, first and second AND-NOT logical elements whose first inputs are connected to the outputs of the first and second pulse shapers respectively, while their second inputs are connected to a H.F. pulse generator and also comprises a least significant decade whose input is connected with the output of the first AND-NOT logical element, a third AND-NOT logical element whose inputs are connected, respectively, to the second AND-NOT logical element and to the least significant decade, a most significant decade whose input is connected to the output of the third AND-NOT logical element, a digital-to-analog converter whose inputs are connected to the first outputs of the least and most significant decades while its output is connected to the second inputs of the first and second null-indicators, and an indicator whose inputs are connected to the other outputs of the least and most significant decades.

It is expedient that the device should incorporate an integrator whose input should be connected to the amplifier unit while the output should be connected directly to the input of the first null-indicator and across a voltage divider to the input of the second null-indicator and that the meter for measuring the parameters of the impact pulse should comprise additionally a control flip-flop whose input should receive an electric signal carrying information about the time of transition through the maximum peak value of the impact pulse, while for measuring the rise and decay areas of the impact pulse it is expedient that the device should incorporate individual units for measuring the rise and decay areas of the impact pulse with their indicators connected to the outputs of the first and third AND-NOT logical elements and to the control flip-flop so that when the latter receives a signal carrying information about the time of transition through the maximum peak value of the impact pulse, the control flip-flip should inhibit the passage of the count pulses carrying information about the rise area of the impact pulse from the first and third AND-NOT logical elements to the unit for measuring the rise area of the impact pulse and should enable the passage of the count pulses carrying information about the decay area of the impact pulse to the unit for measuring the decay area of the impact pulse.

For measuring the rise and decay areas of the impact pulse with a high degree of accuracy it is quite reasonable that each individual unit for measuring rise and the decay areas of the impact pulse should comprise the first and second AND logical elements whose first inputs are connected to the control flip-flop while the second inputs are connected to the outputs of the third and first AND-NOT logical elements, respectively, and the most and least significant decades' inputs are connected, respectively, to the outputs of the first and second AND logical elements while their outputs are connected to the indicator of their area-measuring unit.

Such a design of the device according to the invention ensures measurements of the peak value of an impact pulse of an arbitrary shape and of the total, rise and decay areas of the impact pulse with a high degree of precision. Further, the device according to the invention is noted for high operating speed.

Now the invention will be described in detail by way of examples with reference to the accompanying drawings in which:

FIG. 5 shows the control flip-flop and the functional diagram of the individual units for measuring the rise and decay areas of the impact pulse in the device according to FIG. 2.

FIG. 6 shows space-time diagrams illustrating the operation of the meter for measuring the parameters of the impact pulse in the device according to FIG. 1.

The device for measuring impact pulses according to the invention will be described by illustrating the measurement of several parameters of the impact pulse, such as its peak value and the rise, decay and total areas. Thus, the device shown in FIG. 1 measures the peak value of the impact pulse whereas the device shown in FIG. 2 measures its rise, decay and total areas.

Figure 1:
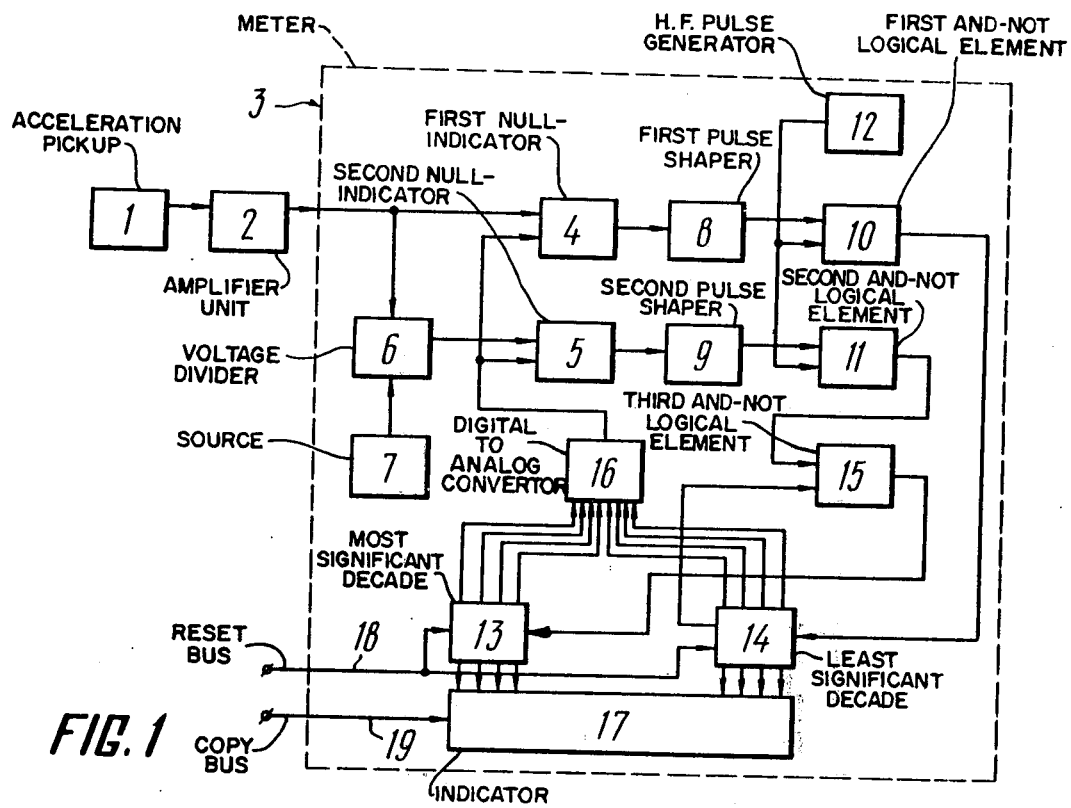
FIG. 1 is a block diagram of the device for measuring impact pulses according to the invention.

The device for measuring impact pulses according to FIG. 1 comprises an acceleration pickup 1 which converts mechanical vibrations of an object into electric signals, said pickup being extensively described elsewhere (see, for example, V.C. Pellinets "Measurements of Impact Accelerations", "Standards" Publishers, 1975, pp 184–190) and is connected across an amplifier unit 2 (same publication, pp 191–204) to a meter 3 for measuring the parameters of the impact pulse.

The meter 3 for measuring the parameters of the impact pulse compares the input signal with the feedback signal, carries out logical processing, converts the analog signal into a digital signal and measures the parameters of the input signal.

The meter 3 for measuring the parameters of the impact pulse comprises, in its turn, first and second null-indicators 4 and 5; one input of the null-indicator 4 is electrically connected with the amplifier unit 2 while one input of the null-indicator 5 is electrically connected with the same amplifier unit 2 across a voltage divider 6 connected to a source 7 of reference voltage extensively described elsewhere (see, for example, V.C. Pellinets "Measurements of Impact Accelerations", "Standards" Publishers, Moscow, 1975, p. 207), first 8 and second 9 pulse shapers whose inputs are connected to the outputs of the null-indicators 4 and 5, respectively, and first and second AND-NOT logical elements 10 and 11 whose first inputs are connected, respectively, to the outputs of the pulse shapers 8 and 9 while their second inputs are connected to a H.F. pulse generator 12. Further, the meter 3 comprises the most significant 13 and least significant 14 decades, the input of the least significant decade 14 being connected with the output of the AND-NOT logical element 10 while the input of the most significant decade 13 is connected with the output of an additional third AND-NOT logical element 15 whose inputs are connected, respectively, to the output of the AND-NOT logical element 11 and to the output of the least significant decade 14, a digital-to-analog converter 16, whose inputs are connected to the first outputs of the least and most significant decades 14 and 13 while its output is connected to the second inputs of the null-indicators 4 and 5, and an indicator 17 whose inputs are connected to the second outputs of the least and most significant decades 14 and 13. The reset pulses of the least and most significant decades 14 and 13 pass through a reset bus 18. The copy pulses pass through a copy bus 19.

In the second version of the device the rise, decay and total areas of the impact pulse are measured with the aid of an additional integrator 20 (FIG. 2) with a control bus 21 realized according to the Author's Certificate No. 469125, Cl. C-06 C-7/18, USSR, while the meter 3 for measuring the parameters of the impact pulse comprises an additional control flip-flop and individual units for measuring the rise area 23 and decay area 24 of the impact pulse, the input of the integrator 20 being connected to the amplifier unit 2 while its output is connected to the input of the null-indicator 4 across a switch 25 and to the null-indicator 5 across the switch 25 and across a voltage divider 6.

The switch 25 is used for connecting the output of the amplifier unit 2 to the meter 3 for measuring the parameters of the impact pulse in the first version and for connecting the integrator 20 to the meter 3 for measuring the parameters of the impact pulse in the second version of the device for measuring the impact pulses.

In the second version of the device the total area of the impact pulse is measured by the same meter 3 but, owing to the fact that the input of the meter 3 receives signals from the integrator 20, the indicator 17 lights up to display the value of the total area of the impact pulse.

The input of the control flip-flop 22 receives a signal through an input bus 26, said signal carrying information about the time of transition through the maximum peak value of the impact pulse while the outputs of the control flip-flop 22 are connected to the individual units for measuring the rise area 23 and decay area 24 of the impact pulse.

The individual units for measuring the rise and decay areas 23 and 24 of the impact pulse are connected to the outputs of the first and third AND-NOT logical elements 10 and 15 and to the control flip-flop 22 so that on receiving the signal carrying information about the time of transition through the maximum peak value of the impact pulse, the control flip-flop inhibits the passage of the count pulses carrying information about the rise area of the impact pulse from the first and third AND-NOT logical elements 10 and 15 to the unit 23 for measuring the rise area of the impact pulse and enables the passage of the count pulses carrying information about the decay area of the impact pulse to the unit 24 for measuring the decay area of the impact pulse.

Each of the units 23 and 24 contains the first and second AND logical elements 27, 28 and 29, 30 whose first inputs are connected in pairs to the outputs of the AND-NOT logical elements 10 and 15 while their second inputs are connected to the outputs of the control flip-flop 22. The outputs of the AND logical elements 27 and 28 are connected to the inputs of the most significant 31 and least significant 32 decades of the unit 23 for measuring the rise area of the impact pulse while the outputs of the AND logical elements 29 and 30 are connected to the inputs of the most significant 33 and least significant 34 decades of the unit 24 for measuring the decay area of the impact pulse. Each individual unit 23 and 24 is provided with indicators 35 and 36 connected, respectively, to the most significant decades 31, 33 and least significant decades 32, 34 of the individual units for measuring the rise area 23 and decay area 24 of the impact pulse.

According to the first version of the device the functional layout of the meter 3 (FIG. 3) for measuring the parameters of the impact pulse comprises two null-indicators 4 and 5 built on series - connected microcircuits 37, 38 and 39, 40, respectively. The input of the second null-indicator 5 is connected to the central point of the voltage divider 6 on resistors 41, 42, one end of the divider being connected to the input of the microcircuit 37 and to the output of the amplifier unit 2, its other end being connected to the source 7 of reference voltage. The outputs of the microcircuits 38 and 40 are connected to the base resistors 43 and 44 of the transistors 45 and 46 of the pulse shapers 8 and 9, respectively. The loading resistors 47 and 48 are connected across the base resistors 49 and 50 to the transistors 51 and 52 of the pulse shapers 8 and 9. Generally, each pulse shaper 8, 9 is a two-stage transistor switch. The loading resistors 53 and 54 of the pulse shapers 8 and 9 are connected to the second inputs of the AND-NOT logical elements 10 and 11. The first inputs of the logical elements 10 and 11 are connected with the H.F. pulse generator 12 comprising three AND-NOT logical elements 55, 56, 57 with a frequency-setting RC-circuit including a resistor 58 and a capacitor 59. The output of the logical element 11 is connected to the first input of the AND-NOT logical element 15 whose second input is connected to the output of the least significant decade 14. The output of the logical element 15 is connected with the input of the most significant decade 13. The second inputs of the microcircuits 37 and 39 of the null-indicators 4 and 5 are connected across the resistors 60, 61 and 62 to the switches 63 of the digital-to-analog converter 16. The inputs of the digital-to-analog converter 16 are connected to the inputs of the switches 63 across buffer stages 64 based on resistors 65, 66, 67 and a transistor 68.

The most significant decade 13 comprises "D" flip-flops 69 and AND logical elements 70 while the least significant decade 14 comprises D flip-flops 71 and AND logical elements 72.

Figure 4:
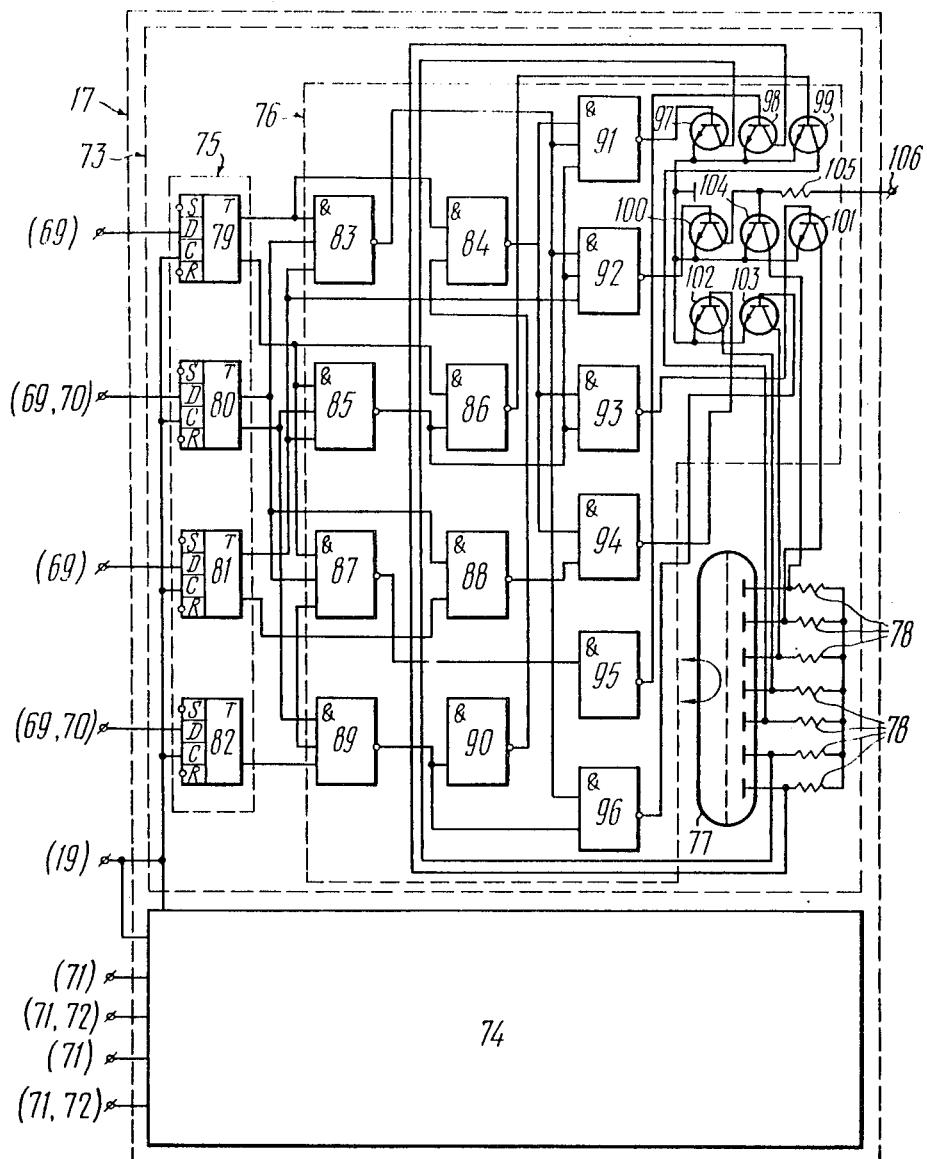
FIG. 4 is a functional diagram of the indicator for measuring the peak value of the impact pulse in the device according to FIG. 1.

The outputs of the most significant 13 and least significant 14 decades are connected to the inputs of the indicator 17 whose functional diagram appears in FIG. 4. The indicator 17 comprises a most significant digit 73 and a least significant digit 74 connected, respectively, to the D flip-flops 69 and AND logical elements 70 of the most significant decade 13 and to the D flip-flops 71 and AND logical elements 72 of the least significant decade 14.

The most significant digit 73 of the indicator 17 comprises a memory register 75, a decoder 76 and an indicator tube 77 with corresponding loading resistors 78. The memory register 75 of the most significant digit of the indicator 17 is based on D flip-flops 79, 80, 81 and 82. The decoder 76 is based on the AND-NOT logical elements 83, 84, 85, 86, 87, 88, 89, 90, 91, 92, 93, 94, 95, 96 and on the transistors 97, 98, 99, 100, 101, 102, 103, 104. One output of the D flip-flop 79 is connected to the first input of the logical elements 83, 84 in the decoder 76 while the other output of the D flip-flop 79 is connected to the first input of the logical elements 85, 86, 87. One output of the D flip-flop 80 is connected to the second input of the logical elements 83 and 87 and to the first input of the logical element 88. The other output of the D flip-flop 80 is connected with the second input of the logical element 85 and with the first of the logical element 89. One output of the D flip-flop 81 is connected with the third input of the logical elements 83, 85, 92. Its other output is connected with the third input of the logical element 87 and with the second input of the logical elements 88 and 89. The output of the flip-flop 82 is connected to the third input of the logical element 89. The output of the logical element 83 is connected to the second input of the logical element 91 and the output of the logical element 85 is connected to the second input of the logical elements 86, 91, 92 and 93. The output of the logical element 87 is connected with the input of the logical element 95 while the output of the logical element 89 is connected with the second input of the logical element 96 and with the input of the logical element 90 whose output is connected with the second input of the logical element 84. The output of the logical element 84 is connected to the first input of the logical elements 91, 93 and 94 while the output of the logical element 88 is connected to the second input of the logical element 94. The outputs of the logical elements 91, 95, 86, 92, 93, 94 and 96 are connected across the transistors 97, 98, 99, 101, 102, 103 and 104 to the anodes of the indicator tube 77. The transistor 100 and resistor 105 are used to invert the signal supplied from the output of the logical element 92 and the decoder 76 is supplied through a bus 106. The least significant digit 74 of the indicator 17 is similar to the most significant digit 73 and is not described here for the sake of clarity.

In the second version of the device for measuring the total area of the impact pulse the meter 3 for measuring the parameters of the impact pulse is made as shown in FIG. 1 while the indicator 17 made as shown in FIG. 4 is intended to register the value of the total area of the impact pulse. The rise and decay areas of the impact pulse are measured by means of the corresponding individual units 23 and 24 for measuring the rise and decay areas of the impact pulse. These units 23 and 24 are similar in design. The unit 23 (FIG. 5) as well as the unit 24 (the figures in parentheses apply to unit 24) comprises AND logical elements 27 (29) and 28 (30)

as well as the most significant decade 31 (33) and the least significant decade 32 (34). The most significant decade 31 (33) and least significant decade 32 (34) are similar to the respective decades 13 and 14 of the meter 3 for measuring the parameters of the impact pulse. The outputs of the most significant 31 (33) and least significant 32 (34) decades are connected to the corresponding indicators 35 (36) of the rise and decay areas of the impact pulse. The indicators 35 and 36 are similar to the indicator 17 shown in FIG. 4 and are not described herein for the sake of clarity. The indicator tubes of the indicators 35 and 36 light up to display the value of the rise and decay areas, respectively, of the impact pulse.

The operating principle of the device for measuring impact pulses according to FIG. 1 will be understood more clearly by studying FIG. 6.

FIG. 6 illustrates the voltage shape of the normalized input impact pulse 107, reset pulses 108, count pulses 109 of the most significant decade 13 (FIG. 1), count pulses 110 of the least significant decade 14 and the voltage 111 at the output of the digital-to-analog converter 16 of the meter 3 for measuring the parameters of the impact pulse.

The device for measuring impact pulses according to the invention, first version, functions as follows.

At the initial stage of operation the pulse 108 (FIG. 6) entering the reset bus 18 (FIG. 1) sets the most significant 13 and least significant 14 count decades to position "0" and the voltage at the output of the digital-to-analog converter 16 is equal to zero.

Figure 3:
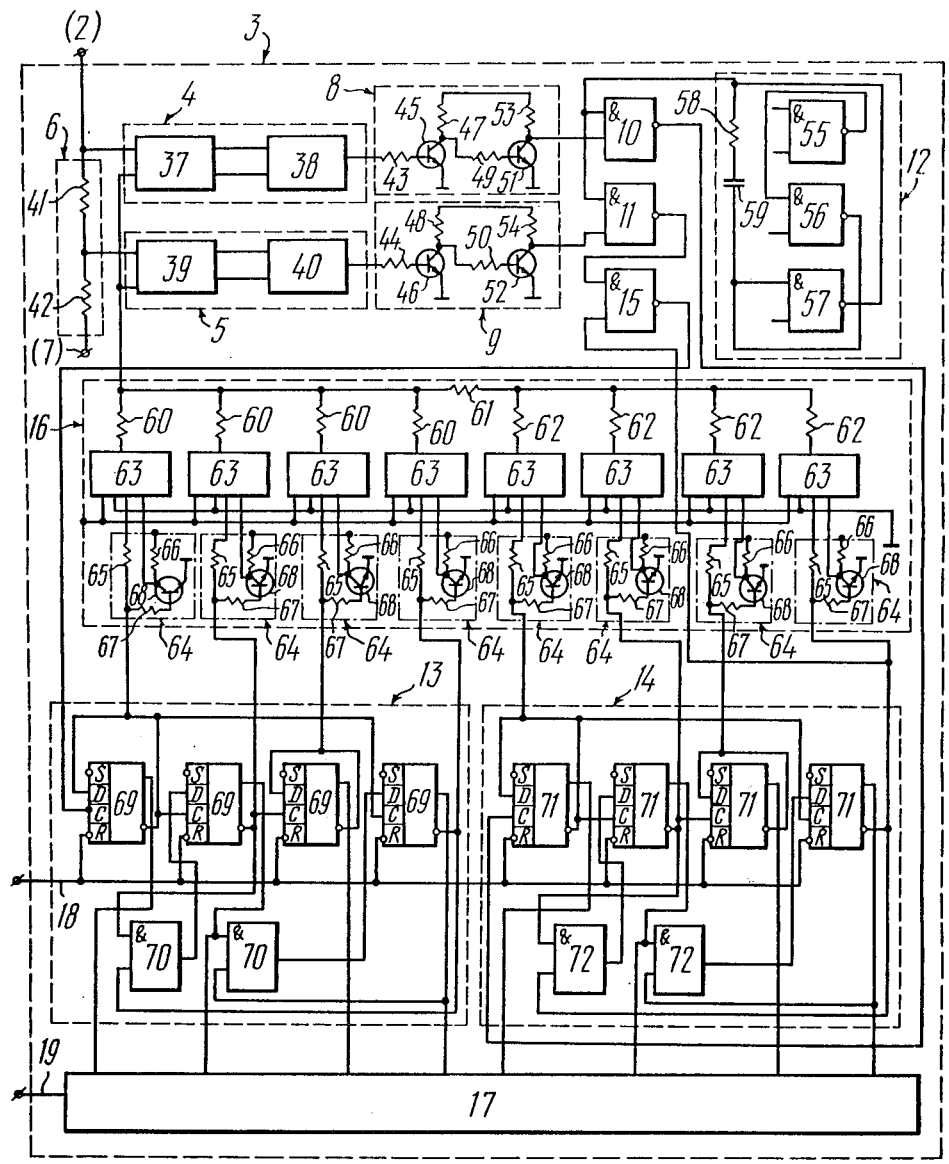
FIG. 3 is a functional diagram of the meter for measuring the parameters of the impact pulse in the device according to FIG. 1.

The electric signal passes from the output of the acceleration pickup 1 installed on the object (not shown in the drawing) to the amplifier unit 2. The output of the amplifier unit 2 generates a normalized signal 107 whose shape follows that of the impact pulse (FIG. 6) and said signal is used in the meter 3 (FIG. 3) measuring the parameters of the impact pulse for further processing and measuring its parameters. This signal enters the first inputs of two null-indicators 4 and 5 whose second inputs receive voltage 111 from the output of the digital-to-analog converter 16. Thus, the null-indicators 4 and 5 compare the voltage 107 (FIG. 6) of the input signal with the voltage 111 at the output of the digital-to-analog converter 16. The normalized signal passes from the output of the amplifier unit 2 directly to the first input of the null-indicator 4 (FIG. 1) while the first input of the null-indicator 5 receives this signal across a voltage divider 6 on resistors 41, 42 (FIG. 3).

Further, the other input of the voltage divider 6, the resistor 42, is connected to the source 7 of reference voltage. As a result, the voltage at the input of the null-indicator 5 is lower than that at the input of the null-indicator 4 by approximately 10 to 15% of the maximum value of the input voltage. If the input voltage of the normalized signal generated by the amplifier unit 2 is sufficiently higher than zero, this will create positive growing pulses at the outputs of the null-indicators 4 and 5. These positive growing pulses enter two series-connected stages based on the transistors 45, 51 and 46, 52, respectively, of the pulse shapers 8 and 9. These stages amplify the input signals and shape the positive pulses which pass from the loading resistors 53 and 54 of the transistors 51 and 52 to the first inputs of the AND-NOT logical elements 10 and 11. The other inputs of the AND-NOT logical elements 10 and 11 receive pulses from the H.F. pulse generator 12. The AND-NOT logical elements 55, 56, 57 of the generator 12 are connected by feedbacks, the input and output of the logical element 57 being connected to a frequency setting RC-circuit consisting of a resistor 58 and a capacitor 59. Such connection of the circuit components ensures stable functioning of the H.F. pulse generator.

The count pulses 110 (FIG. 6) pass from the output of the AND-NOT logical element 10 (FIG. 1) to the input of the least significant decade 14 and the count pulses 109 pass from the output of the logical element 11 to the first input of the AND-NOT logical element 15 whose second input receives count pulses from the inverted output of the least significant decade 14. As a result, the count pulses 109 pass from the output of the logical element 11 to the input of the most significant decade 13. The D flip-flops 69 (FIGS. 3) and the AND logical elements 70 make up the most significant decade 13 whereas the D flip-flops 71 and the AND logical element 72 make up the least significant decade 14. The operation of count decades is widely known from the current literature (see, for example, L.M. Goldenberg "Pulse and Digital Devices", "Svyaz" Publishers, Moscow 1973, p. 460).

The control potentials pass from the outputs of the flip-flops 69 and 71 of the most significant 13 and least significant 14 decades to the inputs of the buffer stages 64 of the digital-to-analog converter 16. The amplified signal passes from the collectors of the transistors 68 of the buffer stages 64 to the switches 63. Simultaneously, the signal from the flip-flops 69 and 71 is delivered through the resistors 65 to the other inputs of the switches 63. In this way the signals generated by the resistors 60 and 62 of the digital-to-analog converter 16 are summed up and enter the second inputs of the null-indicators 4 and 5. The resistor 61 is the connecting resistor of the summing circuit. The voltage 111 (FIG. 6) at the output of the digital-to-analog converter 16 (FIG. 1) keeps rising until it becomes equal to the measured input voltage. In this case the null-indicators 4 and 5 will have negative potentials at the outputs corresponding to a logical zero at the outputs of the pulse shapers 8 and 9 whereas the pulses of the H.F. pulse generator 12 will not reach the inputs of the least significant 14 and most significant 13 decades because the AND-NOT logical elements 10 and 11 are closed.

As the measured input voltage grows, the least significant 14 and most significant 13 decades will again receive pulses until the voltage 111 at the output of the digital-to-analog converter 16 becomes equal to the measured input voltage.

As the measured input voltage diminishes, the count pulses do not pass from the H.F. pulse generator 12 to the least significant 14 and most significant 13 decades so that the voltage at the output of the digital-to-analog converter 16 stays at the previous level up to the moment when the reset bus 18 receives a pulse 108 or the measured input voltage starts growing again and rises higher than the voltage measured earlier.

In order to increase the operating speed of the device, the latter utilizes the principle of parallel transmission of count pulses to the inputs of the least significant 14 and most significant 13 count decades.

Owing to the fact that the input of the null-indicator 5 is provided with a voltage divider 6 it happens that when the growing voltage 111 at the output of the digital-to-analog converter 16 approaches the peak voltage of the normalized input impact pulse 107, first the null-indicator 5 will operate and the count pulses will no longer be sent from the output of the logical element 11 to the input of the logical element 15. Thus, the input of the most significant decade 13 will continue receiving the count pulses 109 only from the output of the least significant decade 14 through the AND-NOT logical element 15.

The ratings of the resistors 41, 42 (FIG. 3) of the voltage divider 6 are selected in such a way that after the count pulses 109 (FIG. 6) stop coming into the most significant decade 13, the input of the least significant decade 14 will receive 10 - 15 more pulses to the moment of voltage comparison.

The results of measurements of the peak value of the impact pulse are read by the indicator 17 (FIG. 4). The signals from the outputs of the D flip-flops 69 of the most significant decade 13 enter the D inputs of the flip-flops 79, 80, 81 and 82 of the memory register 75. The synchronizing inputs "C" of the same flip-flops receive a copy pulse from the bus 19 after which the information is copied from the flip-flops 69 of the most significant decade 13 into the memory register 75 of the most significant digit 73 of the indicator 17. The control potentials coming from the outputs of the flip-flops 79, 80, 81, 82 of the memory register of the most significant digit 73 to the input of the decoder 76 correspond to the information recorded in the memory register 75. The operation of the decoder 76 is widely described in the current literature (see, for example, L.M. Goldenberg "Pulse and Digital Devices", "Svyaz" Publishers, Moscow 1973, p. 462).

The control voltages pass from the collectors of the transistors 97, 98, 99, 101, 102, 103 and 104 of the decoder 76 to the anodes of the indicator tube 77 whose segments light up to display a decimal figure corresponding to the information contained in the memory register 75 of the most significant digit 73 of the indicator 17.

The least significant digit 74 of the indicator 17 functions in a similar way. The indicator tubes of the indicator 17 light up to display the peak value of the impact pulse.

Figure 2:
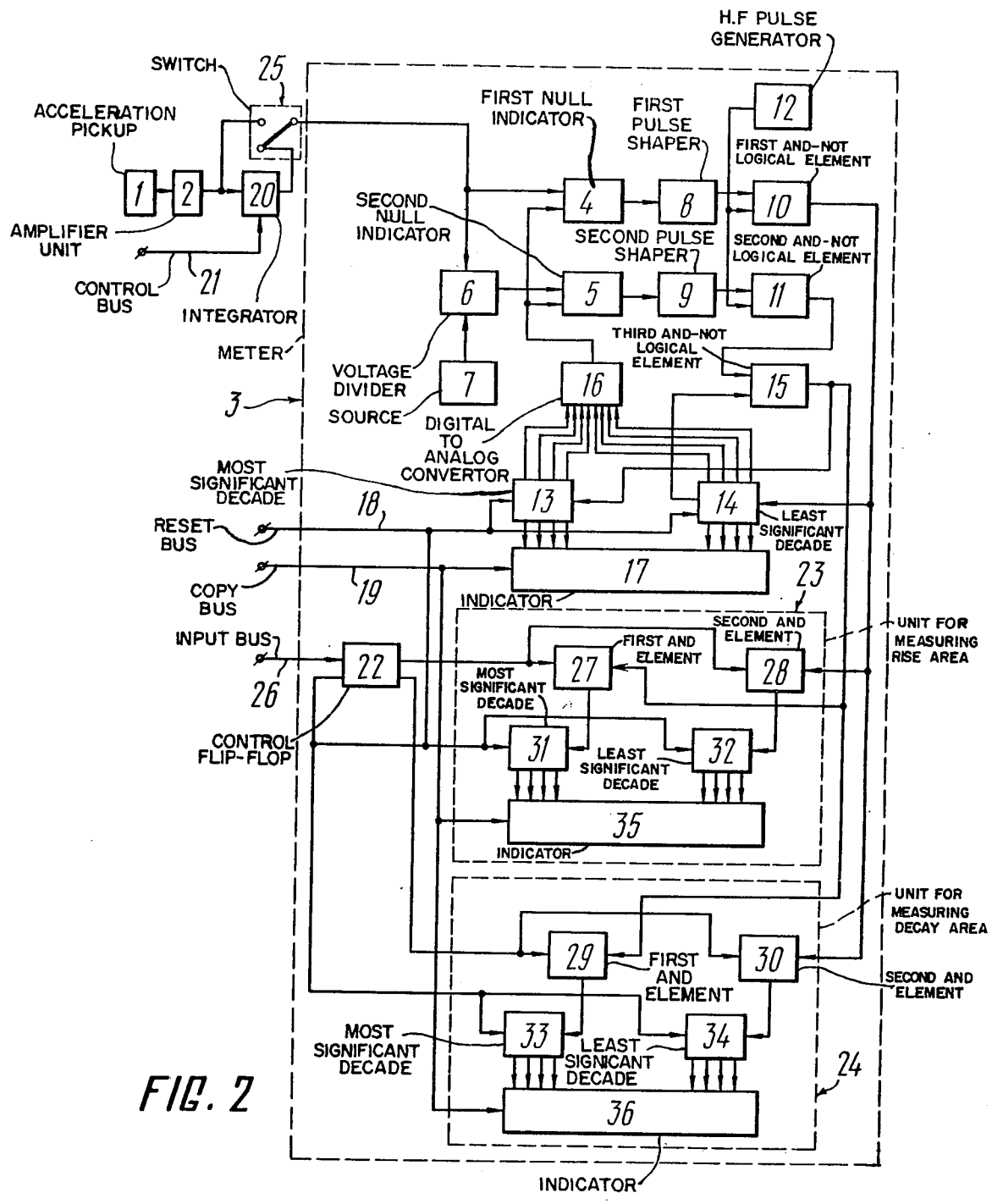
FIG. 2 is a block diagram of another version of the device for measuring impact pulses according to the invention.
Figure 7:
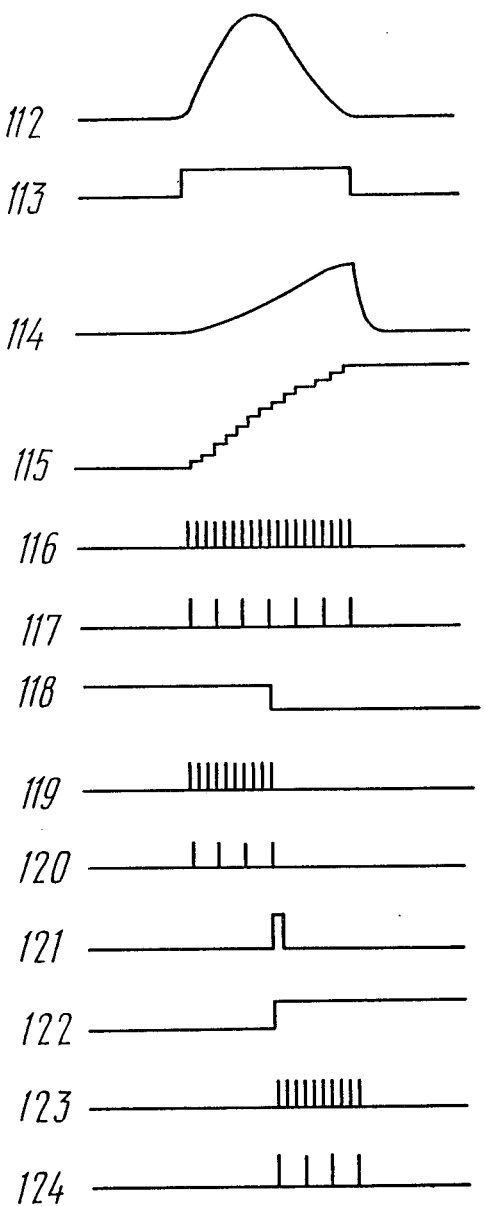
FIG. 7 shows space-time diagrams illustrating the operation of the meter for measuring impact pulses during the measurement of the rise and decay areas of the impact pulse according to FIG. 2.

FIG. 7 is intended to provide for the clearer understanding of the operating principle of the device according to the second version shown in FIG. 2.

Shown in FIG. 7 is the shape of the impact pulse 112, a control pulse 113 delivered to the integrator 20 (FIG. 2), the voltage 114 at the output of the integrator 20, the voltage 115 at the output of the digital-to-analog converter 16, the pulses 116 recorded in the least significant decade 14, the count pulses 117 recorded in the most significant decade 13, the pulse 118 at the output of the control flip-flop 22, the count pulses 119 recorded in the least significant decade 32, the count pulses 120 recorded in the most significant decade 31, the pulse 121 at the input bus 26 of the control flip-flop 22, the pulse 122 at the output of the control flip-flop 22 after the reception of the pulse 121, the count pulses 123 recorded in the least significant decade 34 after the reception of the pulse 121 and the count pulses 124 recorded in the most significant decade 33 after the reception of the pulse 121.

With the purpose of measuring the total area of the impact pulse as well as its rise and decay areas, the amplifier unit 2 (FIG. 2) is connected to the integrator 20 which, in turn, is connected to the pulse parameter meter 3 across the switch 25.

The measured voltage of the normalized impact pulse 112 (FIG. 7) passes from the output of the amplifier unit 2 (FIG. 2) to the input of the integrator 20 whose control bus 21 simultaneously receives a rectangular pulse 113 (FIG. 7) whose duration is equal to that of the measured pulse at the zero level. The voltage 114 (FIG. 7) built up at the output of the integrator 20 (FIG. 2) is proportional to the total area of the measured pulse. The signal from the output of the integrator 20 (FIG. 2) enters the meter 3 for measuring the parameters of the impact pulse and a positive potential 115 (FIG. 7) grows in the digital-to-analog converter 16 of said meter. In this case, in the second version of the device the least significant 14 and most significant 13 decades will record the count pulses 116 and 117 whose number is proportional to the total area of the impact pulse.

In this case the indicator 17 will read the total area of the impact pulse.

Up to the passage of the maximum of the measured normalized signal 112 (FIG. 7) the control flip-flop 22 (FIGS. 2 and 5) has been in a zero state in which case the voltage pulse 118 is delivered from the inverted output of the control flip-flop 22 to the first inputs of the AND logical elements 27 and 28 whose other inputs receive the count pulses from the outputs of the logical elements 10 and 15. The pulses 119 and 120 delivered from the outputs of the AND logical elements 27 and 28 and carrying information about the rise area of the impact pulse in a series-parallel course are delivered to the least significant 32 and most significant 31 decades. After the copy pulse has passed through the bus 19, the indicator 35 will read the value of the impact pulse rise area.

As the maximum of the measured normalized signal 112 (FIG. 7) passes through the input bus 26 (FIG. 5), the input "S" of the control flip-flop 22 receives a pulse 121 which causes the control flip-flop 22 to change its state.

The inputs of the AND logical elements 29, 30 receive a positive pulse 122 from the control flip-flop 22 while the inputs of the AND logical elements 27, 28 have a zero potential. As a result, the count pulses 123 and 124 start passing from the outputs of the logical elements 10 and 15 through the logical elements 29 and 30 to the inputs of the least significant 34 and most significant 33 decades of the individual units 24 for measuring the decay area of the impact pulse. After the copy pulse has passed through the bus 19, the indicator 36 will display the value of the decay area of the impact pulse.

After the end of the impact pulse, the control bus 21 of the integrator 20 receives a zero potential and the integrator 20 is discharged to the zero level.

On completion of the measuring cycle in the second version of the device the three least significant decades 14, 32, 34 (FIG. 2) and most significant decades 13, 31, 33 will record, respectively, the information about the total area of the impact pulse and about its rise and decay areas. This information can be read off the corresponding indicators 17, 35 and 36.

The use of the first and second versions of the device will reduce the scope of measuring equipment required for mechanical tests and for raising the impact strength of various products which will eventually reduce the cost of such tests. Additionally, the device according to the invention raises the precision of measurements and the standard of the test results.

We claim:
1. A device for measuring impact pulses comprising:

an acceleration pickup provided with an output and converting the mechanical vibrations of an object into electric signals;

an amplifier unit with an input and output, said input being connected to said output of said acceleration pickup, said amplifier unit receiving said electric signals coming from said acceleration pickup; and a meter for measuring the parameters of said impact pulse, namely its peak value, having a first input connected to said output of said amplifier unit, said meter receiving electric signals from this amplifier unit and comprising a first null-indicator whose first input serves as said first input of said meter, a voltage divider whose first input serves as a second input of said meter and is also connected to said output of said amplifier unit, a source of reference voltage having an output connected to a second input of said voltage divider, a second null-indicator having its first input connected to an output of said voltage divider, a first pulse shaper having its input connected to an output of the first null-indicator, a second pulse shaper having its input connected to an output of the second null indicator, a first AND-NOT logical element having its first input connected with an output of said first pulse shaper, a second AND-NOT logical element having its first input connected to an output of said second pulse shaper, a H.F. pulse generator having an output connected to a second input of each of said first and second AND-NOT logical elements, a third AND-NOT logical element having its first input connected to an output of the second AND-NOT element, a most significant decade having an input and a group of outputs and being connected to a reset bus and connected by its input with an output of the third AND-NOT logical element, a least significant decade having an input, a first output, a group of outputs and being connected to said reset bus and connected by its input to an output of the first AND-NOT logical element and by the first output to a second input of third AND-NOT logical element, a digital-to-analog convertor having a first and a second group of inputs and an output and connected by its first group of inputs to said group of outputs of said most significant decade, by its second group of inputs to said group of outputs of said least significant decade and by its output to a second input of each of the first and second null-indicators, an indicator, having a first and a second group of inputs and connected to a copy bus, connected by its first and second group of inputs to said groups of outputs of said most significant and least significant decades, respectively, and indicating the measured value of said peak value of said impact pulse.

2. A device for measuring impact pulses comprising:

an acceleration pickup provided with an output and converting the mechanical vibrations of an object into electric signals;

an amplifier unit with an input and an output, said input being connected to said output of said acceleration pickup, said amplifier unit receiving said electric signals coming from said acceleration pickup;

an integrator having an input and an output, connected by its input to said amplifier unit and receiving said electric signals from said amplifier units; and a meter for measuring the parameters of said impact pulse, namely, its total area and the rise and decay areas, having a first input connected to said output of said integrator, said meter receiving said electric signals from this integrator and comprising a first null-indicator whose first input serves as said first input of said meter, a voltage divider whose first input serves as a second input of said meter and is also connected to said output of said integrator, a source of reference voltage having an output connected to a second input of said voltage divider, a second null-indicator having its first input connected to an output of said voltage divider, a first pulse shaper having its input connected to an output of the first null-indicator, a second pulse shaper having its input connected to an output of the second null-indicator, a first AND-NOT logical element having its first input connected with an output of said first pulse shaper, a second AND-NOT logical element having its first input connected to an output of said second pulse shaper, a H.F. pulse generator having an output connected to a second input of each of said first and second AND-NOT logical elements, a third AND-NOT logical element having its first input connected to an output of the second AND-NOT logical element, a most significant decade having an input and a group of outputs and being connected to a reset bus and connected by its input with an output of the third AND-NOT logical element, a least significant decade having an input, a first output, a group of outputs and being connected to said reset bus and connected by its input to an output of the first AND-NOT logical element and by the first output to a second input of the third AND-NOT logical element, a digital-to-analog convertor having a first and a second group of inputs and an output and connected by its first group of inputs to said group of outputs of said most significant decade, by its second group of inputs to said group of outputs of said least significant decade and by its output to a second input of each of the first and second null-indicators, an indicator having a first and a second group of inputs and connected to a copy bus, connected by its first and second groups of inputs to said groups of outputs of said most and least significant decades, respectively, and indicating the measured value of said total area of said impact pulse, a control flip-flop having an input bus and first and second outputs, whose input bus receives an electric signal carrying information about the time of transition through the maximum peak value of said impact pulse, an individual unit for measuring the rise area of said impact pulse having first, second and third inputs and connected by its first and second inputs to outputs of the first and third AND-NOT logical elements, respectively, and by its third input to the first output of said control flip-flop, an individual unit for measuring the decay area of said impact pulse having first, second and third inputs and connected by its first and second inputs to said outputs of the first and third AND-NOT logical elements, respectively, and by the third input to the second output of said control flip-flop so that when the latter receives said signal carrying information about the time of transition through the maximum peak value of said impact pulse, said flip-flop inhibits the passage of count pulses carrying information about said rise area of said impact pulse from the first and third AND-NOT logical elements to said unit for measuring the rise area of the impact pulse and enables the passage of the count pulses carrying information about said decay area of said impact pulse to said unit for measuring the decay area of the impact pulse.

3. A device for measuring impact pulses according to claim 2 wherein each of said individual units for measuring the rise and decay areas of said impact pulse comprises:

a first AND logical element having a first input which serves as a first input of the corresponding units for measuring the rise and decay areas of said impact pulse, a second input which serves as the third input of the corresponding units for measuring the rise and decay areas of said impact pulse and an output, said first AND logical element being connected by its first input to said output of the first AND-NOT logical element and by the second input to the first output of said control flip-flop;

a second AND logical element having a first input which serves as a second input of the corresponding units for measuring the rise and decay areas of said impact pulse, a second input which also serves as the third input of the corresponding units for measuring the rise and decay areas of said impact pulse and an output, said second AND logical element being connected by its first input to said output of the third AND-NOT logical element and by its second input to the first output of said control flip-flop;

a most significant decade having an input and a group of outputs and being connected by its input with said output of said second AND logical element;

a least significant decade having an input and a group of outputs and being connected by its input with said output of said first AND logical element;

an indicator having a first and a second group of inputs and a copy bus and being connected by the first and second groups of inputs to said most and least significant decades, respectively, and indicating the measured value of said rise or decay area of said impact pulse.

4. A device for measuring impact pulses according to claim 2 further comprising: a switch connected electrically with said amplifier unit, with said indicator and with said meter for measuring the parameters of said impact pulse, so that in one position it closes a series circuit with said amplifier unit and said meter for measuring the parameters of said impact pulse, and said meter measures the peak value of said impact pulse, and in the other position it closes a series circuit with said integrator and said meter for measuring the parameters of said impact pulse, and said meter measures the total area of said impact pulse as well as its rise and decay areas.

* * * * *